(12) United States Patent
Katsuki et al.

(10) Patent No.: US 9,702,843 B2
(45) Date of Patent: Jul. 11, 2017

(54) BIOSENSOR INCORPORATING PROTEIN-IMMOBILIZED MEMBRANE AND METHOD OF IMMOBILIZING PROTEIN IN BIOSENSOR

(71) Applicant: ARKRAY, Inc., Kyoto-shi (JP)

(72) Inventors: Koji Katsuki, Kyoto (JP); Hideaki Yamaoka, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 0 days.

(21) Appl. No.: 14/850,576

(22) Filed: Sep. 10, 2015

(65) Prior Publication Data

US 2015/0377818 A1    Dec. 31, 2015

Related U.S. Application Data

(62) Division of application No. 11/920,782, filed as application No. PCT/JP2006/309906 on May 18, 2006, now abandoned.

(30) Foreign Application Priority Data

May 20, 2005    (JP) .................................. 2005-148253

(51) Int. Cl.
   *G01N 27/327*    (2006.01)
   *C07K 14/705*    (2006.01)
   (Continued)

(52) U.S. Cl.
   CPC ....... *G01N 27/3272* (2013.01); *C07K 14/705* (2013.01); *C07K 14/80* (2013.01);
   (Continued)

(58) Field of Classification Search
   CPC ............. G01N 27/3272; G01N 27/327; G01N 27/3271; G01N 2333/80; C07K 14/705;
   (Continued)

(56) References Cited

U.S. PATENT DOCUMENTS 5,650,062 A * 7/1997 Ikeda .................... C12Q 1/001
                                                         204/403.1
6,458,599 B1   10/2002 Huang
(Continued)

FOREIGN PATENT DOCUMENTS

EP    1426757 A1    6/2004
JP    H08-10208 A   1/1996
(Continued)

OTHER PUBLICATIONS

P.L. Edmiston et al., Molecular Orientation Distributions in Protein Films: III. Yeast Cytochrome c Immobilized on Pyridyl Disulfide-Capped Phospholipid Bilayers, Biophysical Journal, vol. 74, pp. 999-1006, (1998).*
(Continued)

*Primary Examiner* — Luan Van
*Assistant Examiner* — Maris R Kessel
(74) *Attorney, Agent, or Firm* — Fox Rothschild LLP

(57) ABSTRACT

The present invention relates to a protein-immobilized membrane (14) including a cell membrane homologous layer (14A) and a protein (14B) immobilized to the cell membrane homologous layer (14A), where the protein contains cytochrome or a cytochrome complex. The present invention also relates to a method for forming a protein-immobilized membrane (14), and an enzyme-immobilized electrode and a biosensor (X1) provided with a protein-immobilized membrane (14). Preferably, the cell membrane homologous layer (14A) may contain a phospholipid polymer, and the protein (14B) may be CyGDH including an α subunit having a glucose dehydrogenase activity and cytochrome C having a function of electron transfer.

21 Claims, 11 Drawing Sheets

(51) Int. Cl.
*C07K 14/80* (2006.01)
*C12N 9/04* (2006.01)
*C12N 11/08* (2006.01)
*C12Q 1/00* (2006.01)
*C12N 11/06* (2006.01)

(52) U.S. Cl.
CPC ............ *C12N 9/0006* (2013.01); *C12N 11/06* (2013.01); *C12N 11/08* (2013.01); *C12Q 1/006* (2013.01); *G01N 2333/80* (2013.01)

(58) Field of Classification Search
CPC .... C07K 14/80; C12N 9/0004; C12N 9/0006; C12N 11/06; C12N 11/08; C12N 11/00; C12N 11/02; C12Q 1/006
See application file for complete search history.

(56) References Cited

U.S. PATENT DOCUMENTS

| | | | |
|---|---|---|---|
| 6,773,563 | B2 | 8/2004 | Matsumoto |
| 7,604,887 | B2 | 10/2009 | Mino et al. |
| 7,713,544 | B2 | 5/2010 | Chaikof et al. |
| 7,741,090 | B2 | 6/2010 | Sode |
| 2006/0035300 | A1 | 2/2006 | Yamaoka et al. |
| 2006/0258959 | A1 | 11/2006 | Sode |
| 2007/0267301 | A1* | 11/2007 | Sode ................ C12N 9/0004 205/777.5 |

FOREIGN PATENT DOCUMENTS

| | | |
|---|---|---|
| JP | 2003-529634 A | 10/2003 |
| JP | 2005-061961 A | 3/2005 |
| WO | 03/106702 A1 | 12/2003 |
| WO | 2005/023111 A1 | 3/2005 |

OTHER PUBLICATIONS

J. J K. Cullison et al., A Study of Cytochrome c Oxidase in Lipid Bilayer Membranes on Electrode Surfaces, Langmuir, pp. 877-882 (1994).*

James F. Rusling, "Enzyme Bioelectrochemistry in Cast Biomembrane-Like Films", Accounts of Chemical Research, vol. 31, No. 6, Jun. 1, 1998, pp. 363-369.

Ghindilis et al., "Enzyme-Catalyzed Direct Electron Transfer: Fundamentals and Analytical Applications", Electroanalysis, vol. 9, No. 9, Jan. 1, 1997, pp. 661-674, VHC Publishers, Inc., US.

Z. Salamon et al., "Interfacial electrochemistry of cytochrome c at a lipid bilayer modified electrode: effect of incorporation of negative charges into the billayer on cyclic voltammetric parameters", Bioelectrochemistry and Bioenergetics, 26 (1991), pp. 321-334, vol. 321.

Okuda et al. (Biosensors and Bioelectronics 18 (2003) 699-704).

Mizutani "Application of enzyme-modified electrodes to biosensors," Bunseki Kagaku, vol. 48, No. 9, pp. 809-821, The Japan Society for Analytical Chemistry, Sep. 1999.

* cited by examiner (a)

Inventive Electrode (b)

Comparative Electrode

BIOSENSOR INCORPORATING PROTEIN-IMMOBILIZED MEMBRANE AND METHOD OF IMMOBILIZING PROTEIN IN BIOSENSOR

CROSS-REFERENCE TO RELATED APPLICATIONS

This present application is a divisional of U.S. patent application Ser. No. 11/920,782, filed Nov. 20, 2007, which is the U.S. National Phase of International Patent Application Serial No. PCT/JP2006/309906, filed May 18, 2006, which claims priority to Japanese Patent Application Serial No. 2005-148253, filed May 20, 2005. The foregoing application are hereby incorporated by reference in their entireties.

TECHNICAL FIELD

The present invention relates to a technique for immobilizing a protein containing cytochrome to an immobilization target material.

BACKGROUND ART

Biosensors designed to analyze a sample by an electrochemical or optical method are widely used. An example of biosensors designed to analyze a sample by an electrochemical method (see Patent Document 1, for example) is a biosensor 9 shown in FIG. 12 of the present application.

The illustrated biosensor 9 includes a substrate 92 formed with a working electrode 90 and a counter electrode 91, and a cover 94 bonded to the substrate via a spacer 93. The biosensor 9 further includes a flow path 95 defined by the substrate 92, the spacer 93 and the cover 94. The flow path 95 is used for moving a sample by capillary force and formed with a reagent portion 96.

The reagent portion 96 connects the ends of the working electrode 90 and the counter electrode 91 and contains oxidoreductase. The oxidoreductase catalyzes the reaction of taking electrons from glucose, for example. The electrons taken from the glucose are supplied to the working electrode 90. The amount of electrons supplied to the working electrode 90 is measured as the responsive current by utilizing the working electrode 90 and the counter electrode 91.

The four methods described below are typical methods for forming a reagent portion 96, i.e., the methods for immobilizing oxidoreductase (see Non-patent document 1, for example).

In the first method, a material liquid containing oxidoreductase is applied to an intended portion of a target, and then the material liquid is dried. In this way, the oxidoreductase is immobilized to the intended portion of the target.

In the second method, oxidoreductase is immobilized to an intended portion of a target by using a cross-linker such as glutaraldehyde.

In a third method, oxidoreductase is contained in a polymer such carboxymethylcellulose (CMC), and then the oxidoreductase immobilized together with the polymer.

In a fourth method, oxidoreductase is dispersed in a conductive material such as a carbon paste, and the resultant paste is applied to an intended portion of a target, to immobilize the oxidoreductase.

However, with the conventional oxidoreductase-immobilizing methods described above, oxidoreductase fails to be immobilized in a manner such that the active sites are oriented (located) to exhibit efficient activity of the oxidoreductase. In other words, the conventional methods have a drawback that the immobilization is not performed with the orientation of the oxidoreductase being controlled. Specifically, with the conventional methods, active sites of oxidoreductase existing adjacent to each other may face each other or proteins may aggregate each other so that the active site exists within the aggregate. As a result, the ratio of the oxidoreductase (active site) which can be utilized efficiently is relatively low. Accordingly, the probability that oxidoreductase comes into contact with a substrate is relatively low, so that the activity of the immobilized oxidoreductase as a whole is low. Thus, to exhibit the intended function of the immobilized oxidoreductase, the amount of oxidoreductase to be loaded needs to be increased, which is disadvantageous in terms of cost. Particularly, since oxidoreductases are generally expensive, the increase in the amount of oxidoreductase to be loaded leads to a considerably disadvantageous cost increase.

Moreover, since the orientation of oxidoreductase cannot be controlled, the ratio of the actually usable oxidoreductase varies among biosensors even when the same amount of oxidoreductase is loaded. As a result, when the conventional immobilization methods which cannot control orientation are employed, the measurement results vary among biosensors.

Further, in the above-described biosensor 9, electrons taken from the substrate at the active site of the oxidoreductase are transferred to the working electrode 90. However, when the orientation of the oxidoreductase is random, the efficiency of electron transfer from the oxidoreductase to the working electrode is poor. Thus, when the immobilization methods by which the orientation of the oxidoreductase becomes random are employed, an electron mediator needs to be added to mediate the electron transfer between the oxidoreductase and the working electrode 90. Therefore, the biosensor 9 provided by immobilizing oxidoreductase by a conventional method is disadvantageous in terms of cost, because it requires an electron mediator. Further, as the electron mediator, metal complexes such as potassium ferrocyanide are used some of which have an adverse effect on the human body. Thus, it is not desirable to use an electron mediator for such an analytical tool as the biosensor 9.

Patent document 1: JP-B-H08-10208

Non-patent document 1: MIZUTANI Fumio, "Application of enzyme-modified electrodes to biosensors," BUNSEKI KAGAKU, Vol. 48, No. 9 pp. 809-821, The Japan Society for Analytical Chemistry, September, 1999.

DISCLOSURE OF THE INVENTION

An object of the present invention is to immobilize a protein such as oxidoreductase with good orientation and to cause the activity to be exhibited efficiently and advantageously in terms of cost with the use of a small amount of enzyme.

Another object of the present invention is to provide a biosensor which is capable of properly measuring the concentration of a substrate such as glucose without using an electron mediator.

According to a first aspect of the present invention, there is provided a protein-immobilized membrane comprising a cell membrane homologous layer, and a protein immobilized to the cell membrane homologous layer, where the protein contains cytochrome or a cytochrome complex.

According to a second aspect of the present invention, there is provided a method for immobilizing a protein. The method comprises a first step of forming a cell membrane homologous layer at an intended portion of an immobilization target member, and a second step of causing self organization of a protein with respect to the cell membrane homologous layer, the protein containing cytochrome or a cytochrome complex.

Preferably, the protein immobilization method according to the present invention further comprises a third step of subjecting the intended portion to hydrophilic treatment before the first step.

According to a third aspect of the present invention, there is provided an enzyme-immobilized electrode comprising a substrate, and an enzyme-containing layer immobilized to the substrate. The enzyme-containing layer includes a cell membrane homologous layer and an enzyme. The enzyme contains, as a subunit, cytochrome C immobilized to the cell membrane homologous layer by self organization.

According to a fourth aspect of the present invention, there is provided a biosensor comprising a substrate, and an enzyme-containing layer immobilized to the substrate. The enzyme-containing layer includes a cell membrane homologous layer and an enzyme. The enzyme contains, as a subunit, cytochrome C immobilized to the cell membrane homologous layer by self organization.

The biosensor according to the present invention may further comprise a flow path for moving a sample, and a reagent portion provided in the flow path.

The biosensor according to the present invention may further comprise a working electrode and a counter electrode which are partially exposed at the flow path and utilized for applying a voltage to a sample. In this case, at least part of the cell membrane homologous layer is formed on the working electrode.

The reagent portion may contain a color former. In this case, the reagent portion may include a chromogenic layer containing a color former, a cell membrane homologous layer, and a layer containing an enzyme.

The cell membrane homologous layer in the present invention may contain a phospholipid polymer. As the phospholipid polymer, it is preferable to use 2-methacryloyloxyethyl phosphorylcholine polymer.

Preferably, the cell membrane homologous layer in the present invention contains a silane coupling agent. As the silane coupling agent, it is preferable to use tetraethoxysilane.

The protein such as an enzyme in the present invention is CyGDH containing an a subunit having a glucose dehydrogenase activity and cytochrome C having a function of electron transfer.

EXPLANATIONS OF REFERENCE SIGNS

X1, X2: Biosensors
1, 5: Substrates (of a biosensor)
11: Working electrode (of a biosensor)
12: Counter electrode (of a biosensor)
14, 51: Reagent portions (of a biosensor)
14A, 50B: Cell membrane homologous layers (of a reagent portion)
14B, 50C: CyGDH layers (of a reagent portion)
4, 8: Capillaries (flow paths)
51A: Chromogenic layer (of a reagent portion)

BEST MODE FOR CARRYING OUT THE INVENTION

Preferred embodiments of the present invention will be described below, as first and second embodiments, with reference to the accompanying drawings.

The first embodiment of the present invention will be described below with reference to FIGS. 1-3.

Figure 1:
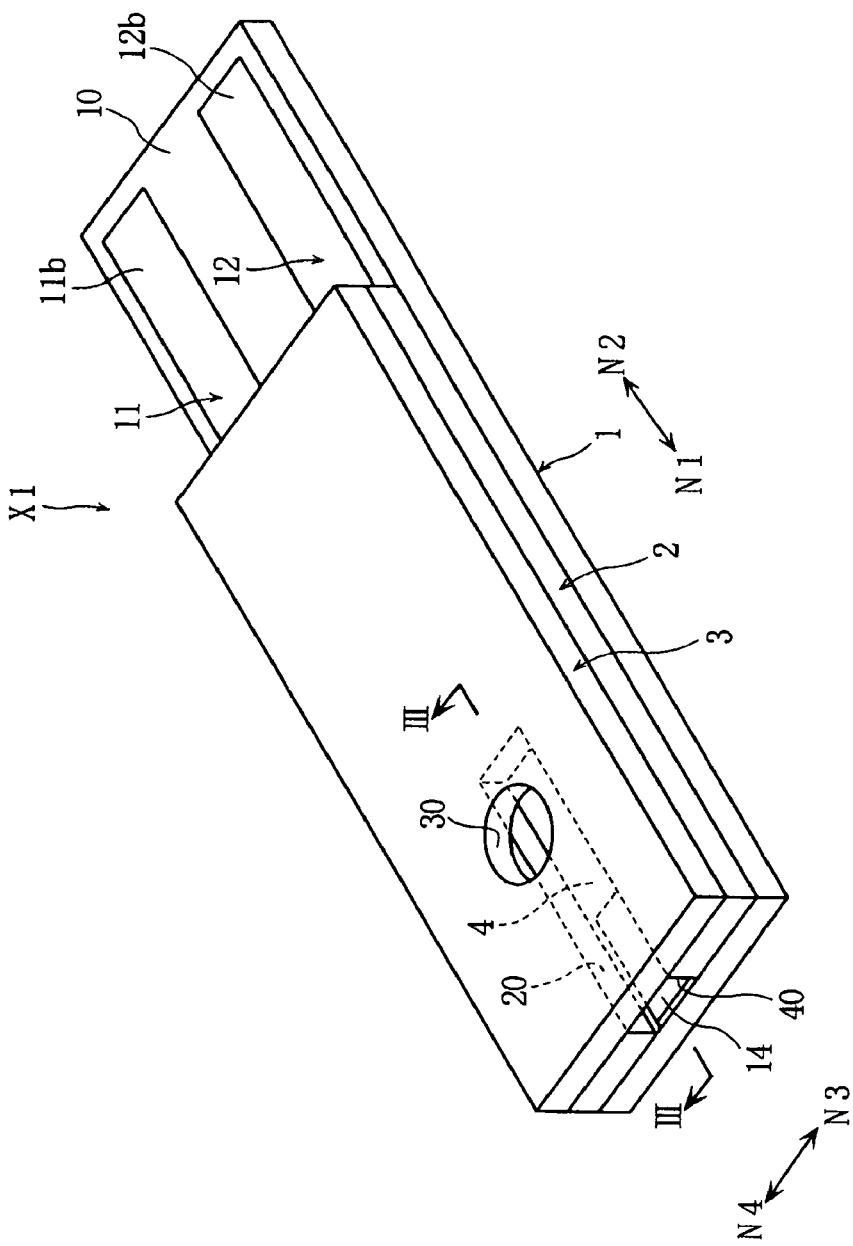
FIG. 1 is an overall perspective view showing a biosensor according to a first embodiment of the present invention.
Figure 2:
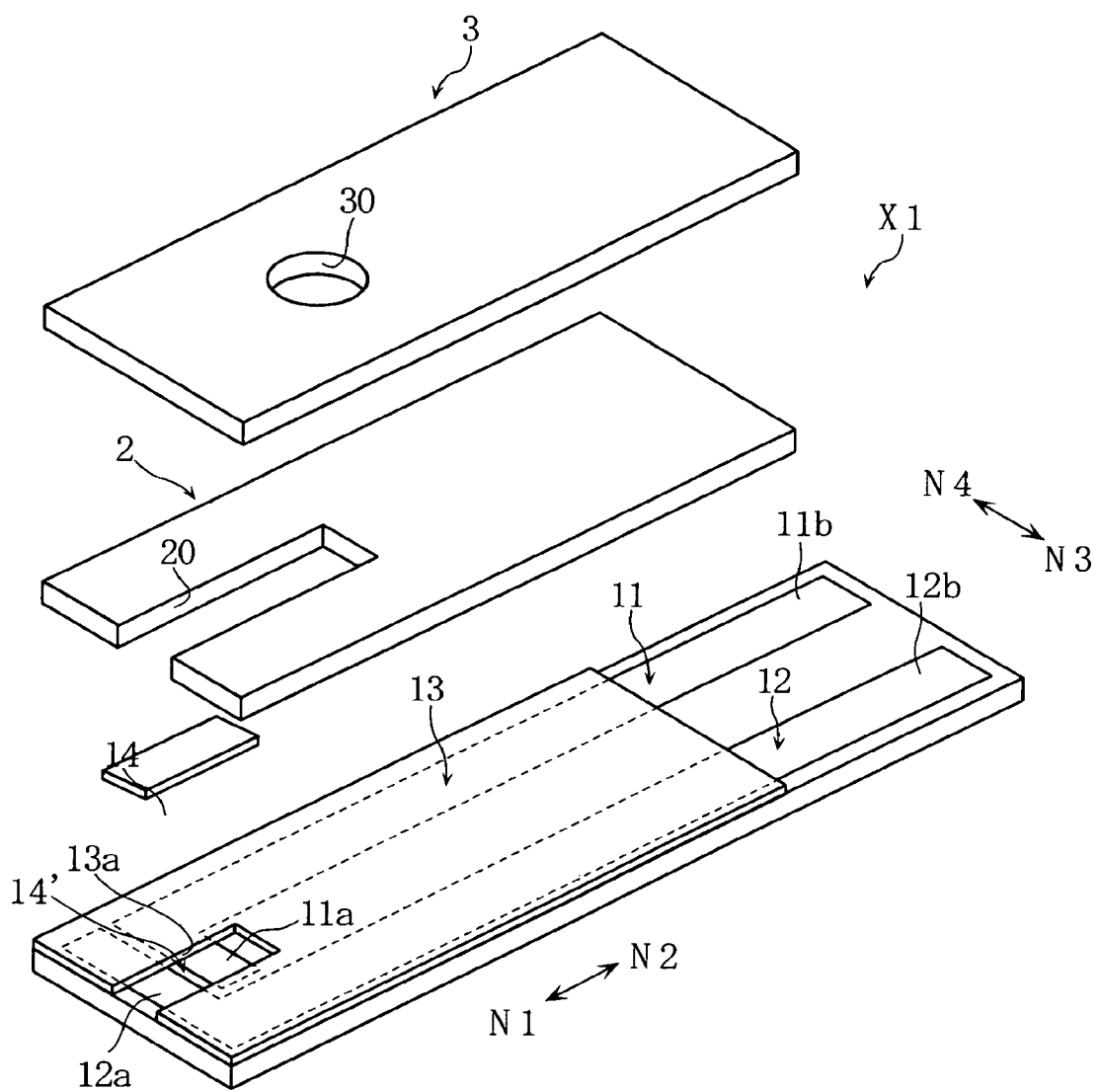
FIG. 2 is an exploded perspective view of the biosensor shown in FIG. 1.
Figure 3:
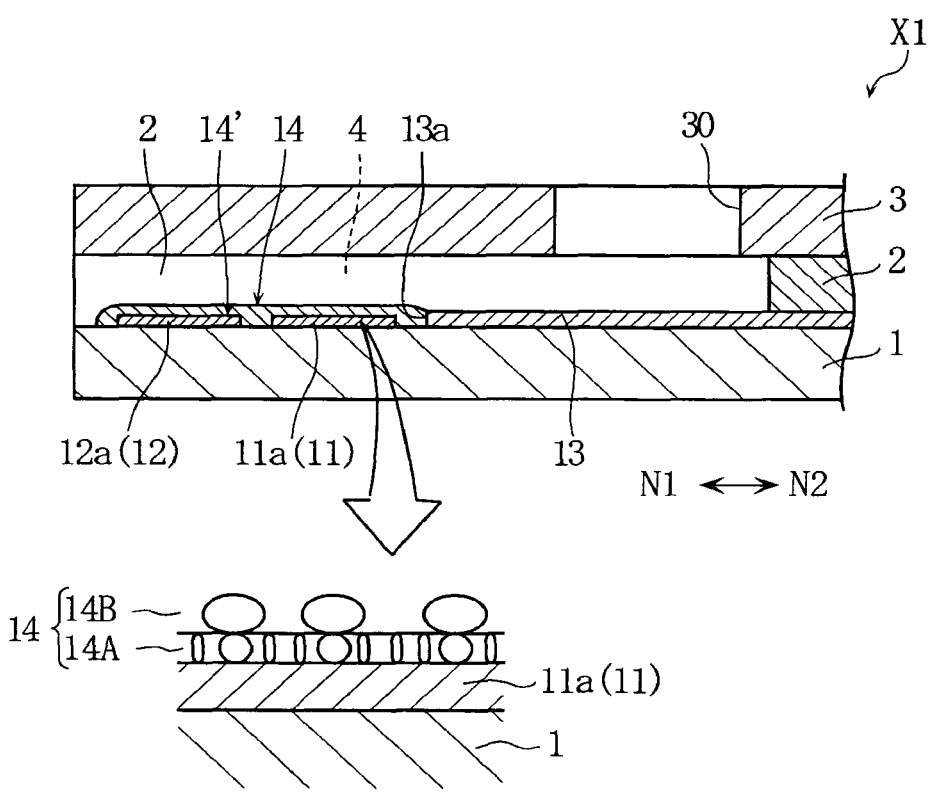
FIG. 3 is a sectional view taken along lines in FIG. 1, a principal portion of which is shown as enlarged.

The biosensor X1 shown in FIGS. 1-3 is a disposable sensor to be mounted to a concentration measuring apparatus (not shown) to measure a blood glucose level. The biosensor X1 is adapted to measure the blood glucose level by an electrochemical method and includes a substrate 1, which is in the form of an elongated rectangle, and a cover 3 laminated on the substrate via a spacer 2. In the biosensor X1, a capillary 4 extending in the longitudinal direction of the substrate 1 (N1, N2 directions in the figures) is defined by the elements 1-3. The capillary 4 is utilized for moving the blood introduced from an introduction port 40 in the longitudinal direction of the substrate 1 (N1, N2 directions in the figures) utilizing capillary action and retaining the introduced blood.

The spacer 2 defines the distance from the upper surface 10 of the substrate 1 to the lower surface 30 of the cover 3, i.e., the height of the capillary 4 and may comprise a double-sided tape. The spacer 2 is formed with a slit 20 having an open end. The slit 20 defines the width of the capillary 4. The open end of the slid 20 serves as the introduction port 40 for introducing blood into the capillary 4.

The cover 3 includes an exhaust port 30 for discharging gas from the capillary 4. The cover 3 is made of a thermoplastic resin having a high wettability, such as Vinylon or highly crystalline PVA.

As shown in FIGS. 2 and 3, the upper surface 10 of the substrate 1, which is made of an insulating resin such as PET, is formed with a working electrode 11, a counter electrode 12, an insulating film 13 and a reagent portion 14.

Each of the working electrode 11 and the counter electrode 12 is L-shaped as a whole. Specifically, the working electrode 11 and the counter electrode 12 mostly extend in the longitudinal direction of the substrate 1 (N1, N2 directions in the figures) and respectively include ends 11a and 12a extending in the width direction (N3, N4 directions in the figures). The working electrode 11 and the counter electrode 12 further include ends 11b and 12b, respectively, which provide terminals for coming into contact with the terminals of the concentration measuring apparatus (not shown). The working electrode 11 and the counter electrode 12 may be formed by screen printing using carbon paste. The working electrode 11 and the counter electrode 12 may be made of a conductive material other than carbon by spin coating, thermal transfer, carbon rod slice, vapor deposition, sputtering or CVD.

The insulating film 13 covers most part of the working electrode 11 and the counter electrode 12 while exposing the ends 11a, 12a, 11b and 12b of the working electrode 11 and the counter electrode 12. The insulating film 13 includes an opening 13a for exposing the ends 11a and 12a of the working electrode 11 and the counter electrode 12. The opening 13a defines the region for forming the reagent portion 14 and is in the form of a rectangle elongated in the longitudinal direction of the substrate 1 (N1, N2 directions in the figures).

The insulating film 13 may be formed by screen printing using ink containing a material having high water repellency or photolithography using a photosensitive resin.

The reagent portion 14 is arranged to bridge the ends 11a and 12a of the working electrode 11 and the counter electrode 12 at the opening 13a of the insulating film 13. The reagent portion 14 includes a cell membrane homologous layer 14A and a CyGDH layer 14B.

The cell membrane homologous layer 14A is utilized for immobilizing CyGDH with controlled orientation. The cell membrane homologous layer 14A may be formed by applying a solution containing phospholipid polymer to the portion 14' of the working electrode 11 and the counter electrode 12 which is exposed through the opening 13a of the insulating film 13 (hereinafter, the portion 14' is referred to as "exposed portion 14'") and then drying the solution.

As the phospholipid polymer, use may b made of 2-methacryloyloxyethyl phosphorylcholine (MPC) polymer, for example. As the MPC polymer, use may be made of one prepared by polymerizing MPC alone or one prepared by copolymerizing MPC with a hydrophobic monomer such as methacrylate (e.g. butyl methacrylate).

As the phospholipid polymer for forming the cell membrane homologous layer 14A, polymers other than MPC polymer may be used as long as the polymer contains a monomeric unit having a structure similar to phospholipid forming a cell membrane in the molecules.

As the phospholipid polymer, it is preferable to use one to which a silane coupling agent is added. In this case, the phospholipid polymer is reliably bonded to the exposed portion 14'.

To form the cell membrane homologous layer 14A, it is preferable to subject the exposed portion 14' to hydrophilic treatment in advance. By this treatment, hydrophilic groups such as a hydroxyl group or a carboxyl group enters the exposed portion 14' and is bonded to the silane coupling agent. Thus, phospholipid polymer is more strongly fixed to the exposed portion 14'.

The amount of the silane coupling agent in the polymer may be set to 10 to 500 parts by weight relative to 100 parts by weight of the polymer component. Examples of silane coupling agent include: tetraethoxysilane; vinyltrichlorosilane; vinyl-tris(2-methoxyethoxy) silane; γ-methacryloxypropyltrimethoxysilane; γ-methacryloxypropyltriethoxysilane; β-(3,4-epoxycyclohexyl)ethyltrimethoxysilane; γ-glycidoxypropyltriethoxysilane; γ-aminopropyltriethoxysilane; N-phenyl-γ-aminopropyltrimethoxysilane; γ-chloropropyltrimethoxysilane; and γ-mercaptopropyltrimethoxysilane. These silane coupling agents may be used solely or in combination.

The hydrophilic treatment of the exposed portion 14' can be performed by various known techniques. Examples of hydrophilic treatment which can be employed in the present invention include VUV treatment, UV treatment, corona discharge and plasma treatment.

The CyGDH layer 14B is provided by immobilizing CyGDH self-organizingly to the cell membrane homologous layer 14A. Although FIG. 3 shows the state in which CyGDH is immobilized to the surface of the cell membrane homologous layer 14A, this figure is a schematic view for describing the present invention. Thus, although the inventors of the present invention have ascertained that CyGDH is self-organizingly immobilized to the cell membrane homologous layer 14A, the inventors have not yet found out how CyGDH is immobilized to the cell membrane homologous layer 14A. Further, CyGDH derived from a microorganism belonging to the *burkhorderia cepacia*, which will be described later, is a transmembrane protein. Therefore, CyGDH may not be immobilized only at the surface of the cell membrane homologous layer 14A, as shown in FIG. 3, but may be immobilized to the cell membrane homologous layer 14A while penetrating the cell membrane homologous layer 14A.

The self-organizing immobilization of CyGDH to the cell membrane homologous layer 14A may be performed by immersing the substrate 1 provided with the cell membrane homologous layer 14A at the exposed portion 14' into an enzyme solution containing CyGDH or spraying the enzyme solution to the cell membrane homologous layer 14A and then drying the solution.

As will be understood from the AFM image (see FIG. 8) to be described later, when CyGDH is self-organizingly immobilized to the cell membrane homologous layer 14A, CyGDH is immobilized with controlled orientation. Specifically, CyGDH is so immobilized to the cell membrane homologous layer 14A that the active site of the a subunit is positioned at the surface of the reagent portion 14, whereas cytochrome C is positioned close to or in contact with the exposed portion 14' (working electrode 11).

In the present invention, as the CyGDH, use is made of those which at least contain an a subunit having a glucose dehydrogenase activity and cytochrome C having a function of electron transfer. Thus, CyGDH further containing a subunit other than a subunit and cytochrome C may be used. Examples of such CyGDH are disclosed in international publication WO02/36779. The CyGDH disclosed in this international publication is derived from a microorganism belonging to the *burkholderia cepacia* and includes an a subunit having a molecular weight of about 60 kDa in SDS-polyacrylamide gel electrophoresis under a reduced condition, including FAD as a cofactor and having a glucose dehydrogenase activity, and cytochrome C having a molecular weight of about 43 kDa in SDS-polyacrylamide gel electrophoresis under a reduced condition and having a function of electron transfer. The CyGDH in the present invention further includes one prepared by utilizing a transformant to which a gene encoding CyGDH taken from a microorganism belonging to the *burkholderia cepacia* is transferred.

The CyGDH derived from a microorganism belonging to the *burkhorderia cepacia* is a transmembrane protein. That is, the CyGDH derived from this microorganism originally exists in a cell membrane. Thus, when such CyGDH is used, CyGDH is immobilized to the cell membrane homologous layer 14A by self organization with controlled orientation similarly to that in existing in a cell membrane. Such self-organizing immobilization of CyGDH is possible not only when CyGDH derived from a microorganism belonging to the *burkhorderia cepacia* is used but also when CyGDH originally existing in a cell membrane is used.

When the biosensor X1 having the above-described structure is mounted to a concentration measuring apparatus (not shown) and blood is introduced to the capillary 4 through the introduction port 40 of the biosensor X1, the blood glucose level is measured automatically at the concentration measuring apparatus (not shown).

The introduction of blood to the biosensor X1 may be performed either before or after the biosensor is mounted to the concentration measuring apparatus (not shown). Generally, blood is introduced by cutting the skin of the person to be tested to cause bleeding and then applying the blood to the introduction port 40 of the biosensor X1.

When the biosensor X1 is mounted to the concentration measuring apparatus (not shown), the working electrode 11 and the counter electrode 12 of the biosensor X1 come into contact with the terminals (not shown) of the concentration measuring apparatus. In the biosensor X1, the blood applied to the introduction port 40 moves toward the exhaust port 30 due to capillary action at the capillary 4 and fills the capillary 4.

In the capillary 4, CyGDH reacts specifically with the glucose in the blood to take electrons from the glucose. When a voltage is applied to the blood using the working electrode 11 and the counter electrode 12, the electrons taken out by the CyGDH are transferred to the working electrode 11. In the concentration measuring apparatus (not shown), when a voltage is applied to the working electrode 11 and the counter electrode 12, the amount of electrons transferred to the working electrode 11, for example, is measured as the responsive current. Based on the responsive current, the blood glucose level is computed.

In the biosensor X1, CyGDH is immobilized with controlled orientation so that the active site of the a subunit is positioned at the surface of the reagent portion 14. Thus, in the reagent portion 14, electrons are efficiently taken from glucose. As a result, in the biosensor X1, intended activity is properly exhibited even with the use of a relatively small amount of CyGDH, which is advantageous in terms of cost.

Since CyGDH is immobilized with controlled orientation, the amount of CyGDH contained in the reagent portion 14 and the orientation (position) of the active site do not vary among biosensors X1. Thus, variation in sensitivity among the biosensors X1 does not occur, so that the blood glucose level measurement is performed properly.

Since CyGDH is immobilized with controlled orientation in the biosensor X1, cytochrome C exists close to or in contact with the exposed portion 14' (working electrode 11). Thus, in the reagent portion 14, electrons taken from the glucose are efficiently transferred to the working electrode 11. Thus, in the biosensor X1, proper responsive current is obtained without using an electron mediator such as a metal complex.

A second embodiment of the present invention will be described below with reference to FIGS. 4 and 5.

Figure 4:
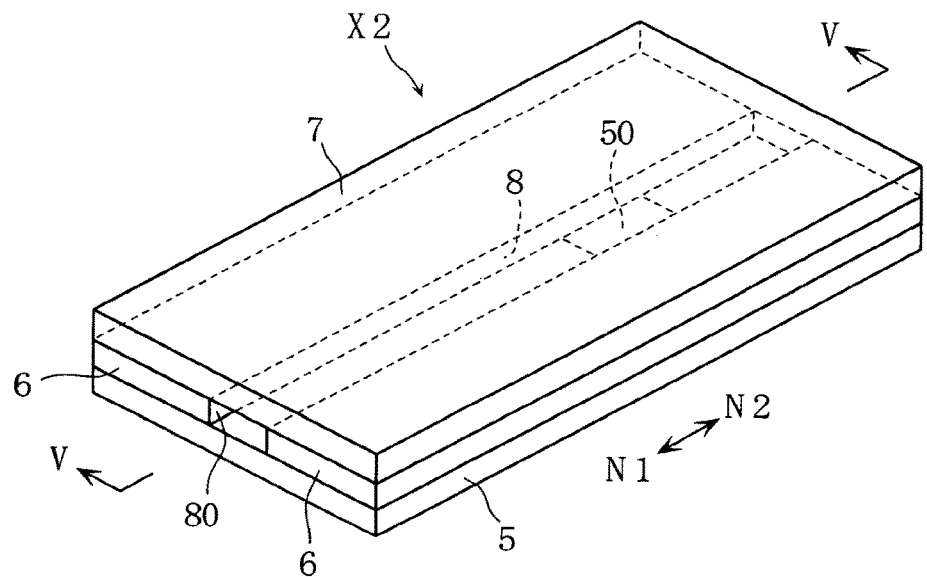
FIG. 4 is an overall perspective view showing a biosensor according to a second embodiment of the present invention.
Figure 5:
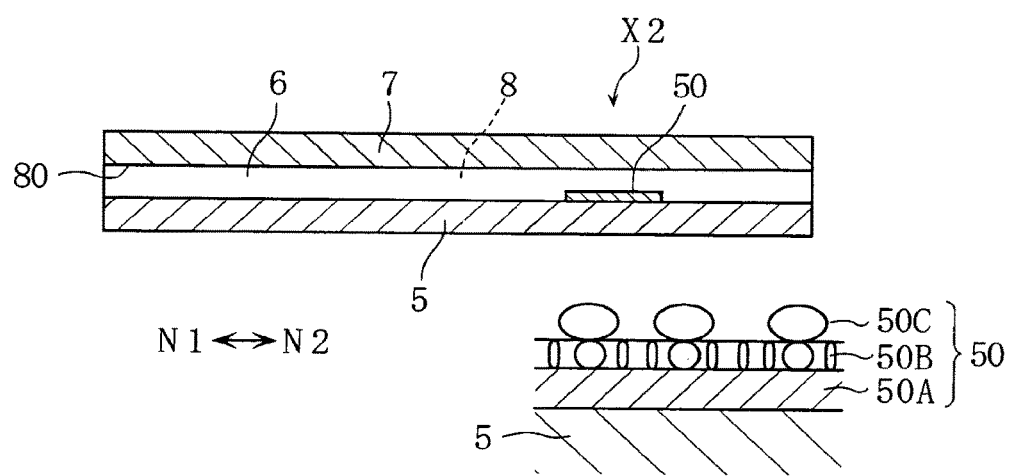
FIG. 5 is a sectional view taken along lines V-V in FIG. 4, a principal portion of which is shown as enlarged.

Unlike the foregoing biosensor X1 (see FIGS. 1-3), the biosensor X2 shown in FIGS. 4 and 5 is adapted to measure the blood glucose level by an optical method.

The biosensor X2 includes a substrate 5, which is in the form of an elongated rectangle, and a cover 7 laminated on the substrate via a pair of spacers 6. In the biosensor X2, a capillary 8 extending in the longitudinal direction of the substrate 5 (N1, N2 directions in the figures) is defined by the elements 5-7. The capillary 8 is used for moving the blood introduced from an introduction port 80 in the longitudinal direction of the substrate 5 (N1, N2 directions in the figures) utilizing capillary action and retaining the introduced blood.

A reagent portion 51 is provided in the capillary 8. The reagent portion 51 includes a chromogenic layer 51A, and a cell membrane homologous layer 51B and a CyGDH layer 51C which are formed on the chromogenic layer 51A.

The chromogenic layer 51A includes a color former and may be formed by applying a solution containing a color former to an intended portion of the substrate 5 and then drying the solution.

Examples of color former which can be used in the present invention include:
MTT(3-(4,5-Dimethyl-2-thiazolyl)-2,5-diphenyl-2H-tetrazolium bromide);
INT(2-(4-lodophenyl)-3-(4-nitrophenyl)-5-phenyl-2H-tetrazolium chloride);
WST-4(2-(4-lodophenyl)-3-(2,4-dinitrophenyl)-5-(2,4-disulfophenyl)-2H-tetrazolium,monosodium salt); and
4AA(4-Aminoantipyrine).

The cell membrane homologous layer 51B and the CyGDH layer 51C can be formed similarly to those of the foregoing biosensor X1 (see FIGS. 1-3).

In this biosensor X2 again, the reagent portion 51 includes a cell membrane homologous layer 51B and a CyGDH layer 51C, similarly to the biosensor X1 (see FIGS. 1-3). Further, the cell membrane homologous layer 51B is held in contact with the chromogenic layer 51A. Thus, in the reagent portion 51, CyGDH is immobilized with controlled orientation, i.e., with the active site of the a subunit positioned at the surface whereas cytochrome C is positioned in contact with or close to chromogenic layer 51A. Thus, the biosensor X2 has the same advantages as those of the biosensor X1 (see FIGS. 1-3).

The present invention is not limited to the foregoing embodiments and may be modified in various ways. For instance, the present invention is not limited to a disposable biosensor and is also applicable to a biosensor used for monitoring the blood glucose level with at least the electrode portion embedded in the human body. The invention is also applicable to a biosensor for measuring the concentration of a substrate other than glucose or to an enzyme electrode for measuring the concentration of a substrate such as glucose.

Example 1

In this example, a carbon electrode, a phospholipid polymer layer and a CyGDH layer were formed on a surface of a PET substrate. The conditions of the surface before and after the formation of these layers were observed using an atomic force microscope (AFM) (Tradename "D-3100" available from Digital Instruments).

(Observation of the Carbon Electrode Surface)

Figure 6:
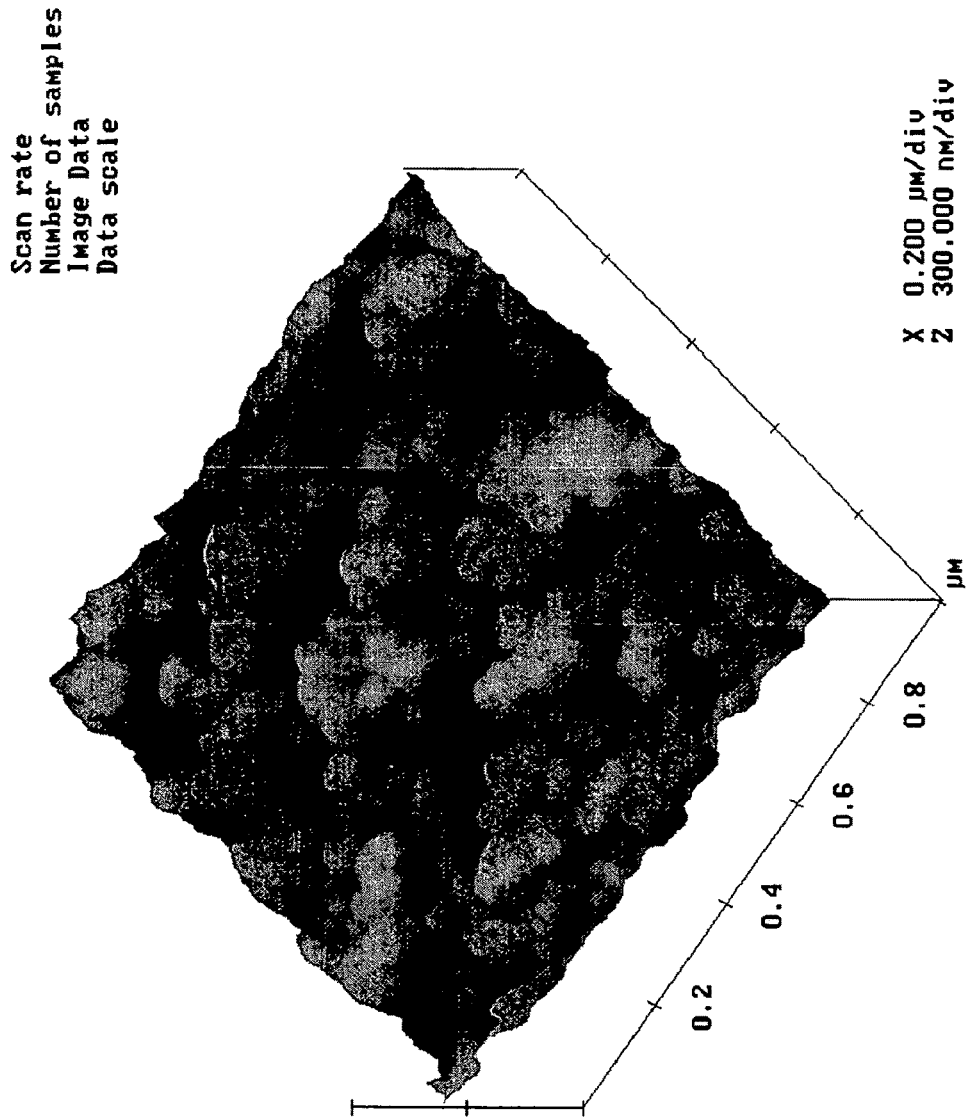
FIG. 6 is an AFM image showing the observation results of the surface condition of a carbon electrode using an AFM in Example 1.

The carbon electrode was formed by screen printing using a carbon ink available from Acheson Japan Ltd. The AFM image of the carbon electrode is shown in FIG. 6. As will be understood from FIG. 6, the surface of the carbon electrode had relatively large irregularities, with carbon particles (having average particle size of about 100 nm) appearing on the surface.

(Observation of the Phospholipid Polymer Layer Surface)

To form the phospholipid polymer layer, the surface of the carbon electrode was first subjected to VUV treatment (hydrophilic treatment). Then, MPC polymer solution was applied to the surface of the carbon electrode and then dried, whereby the phospholipid polymer layer was formed. The VUV treatment was performed by irradiating the surface of the carbon electrode with excimer laser having a wavelength of 172 nm in the atmosphere for 180 seconds with the irradiation distance of 1 mm by using "MECL-M3-750" (available from M. D. Excimer Inc.). As the MPC polymer solution, use was made of a solution of MPC polymer containing tetraethoxysilane as a silane coupling agent (Tradename "LIPIDURER" available from NOF CORPORATION).

Figure 7:
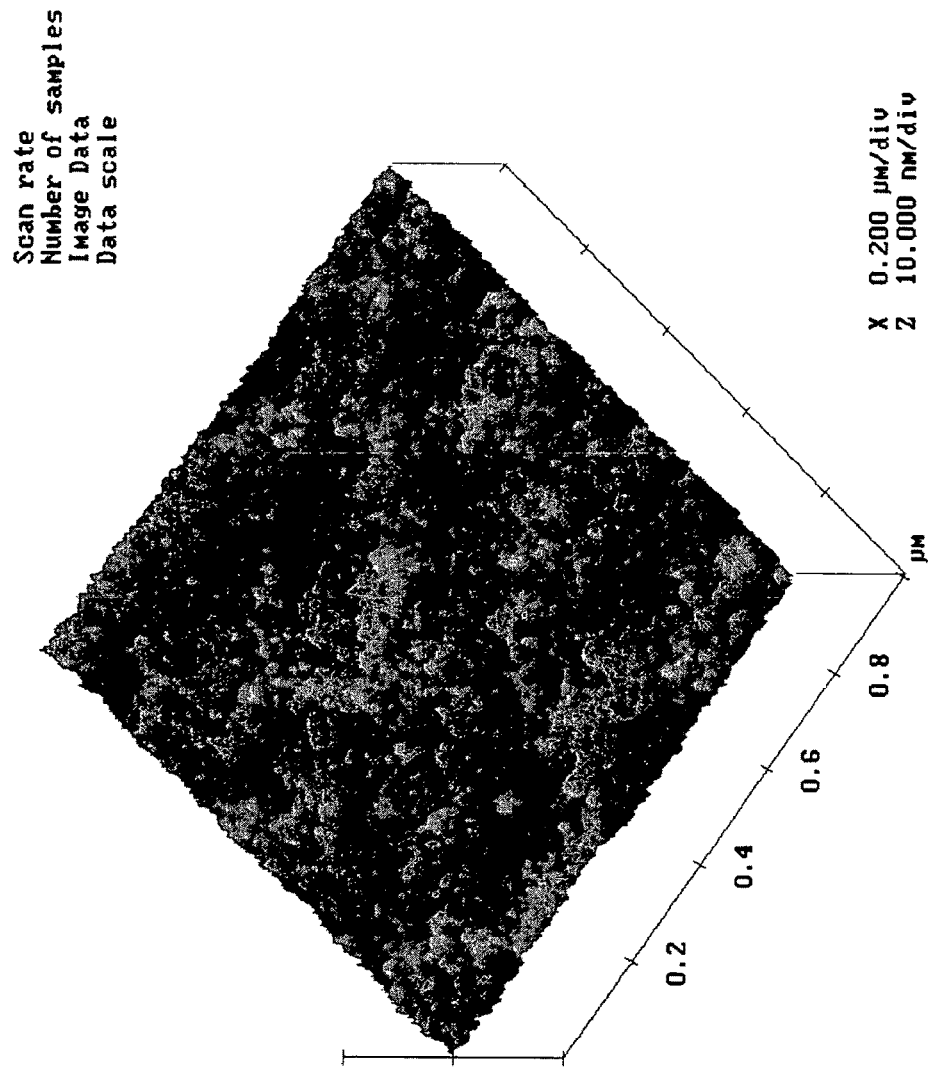
FIG. 7 is an AFM image showing the observation results of the condition of a phospholipid polymer layer formed on the carbon electrode surface using an AFM in Example 1.

The AFM image after the formation of the phospholipid polymer layer was shown in FIG. 7. As will be understood from FIG. 7, although the phospholipid portion of the polymer appeared on the surface of the phospholipid polymer layer, the surface of the phospholipid polymer was smooth as compared with that of the carbon electrode layer (see FIG. 6), because, the diameter of the phospholipid portion was about 2 to 3 nm which was smaller than that of carbon particles.

(Observation of the CyGDH Layer Surface)

The CyGDH layer was formed by immersing the carbon electrode formed' with the phospholipid polymer layer in a CyGDH solution for ten minutes. The concentration of CyGDH in the CyGDH solution was 100 U/µL on the activity basis. The AFM image after the formation of the CyGDH layer is shown in FIG. 8.

Figure 8:
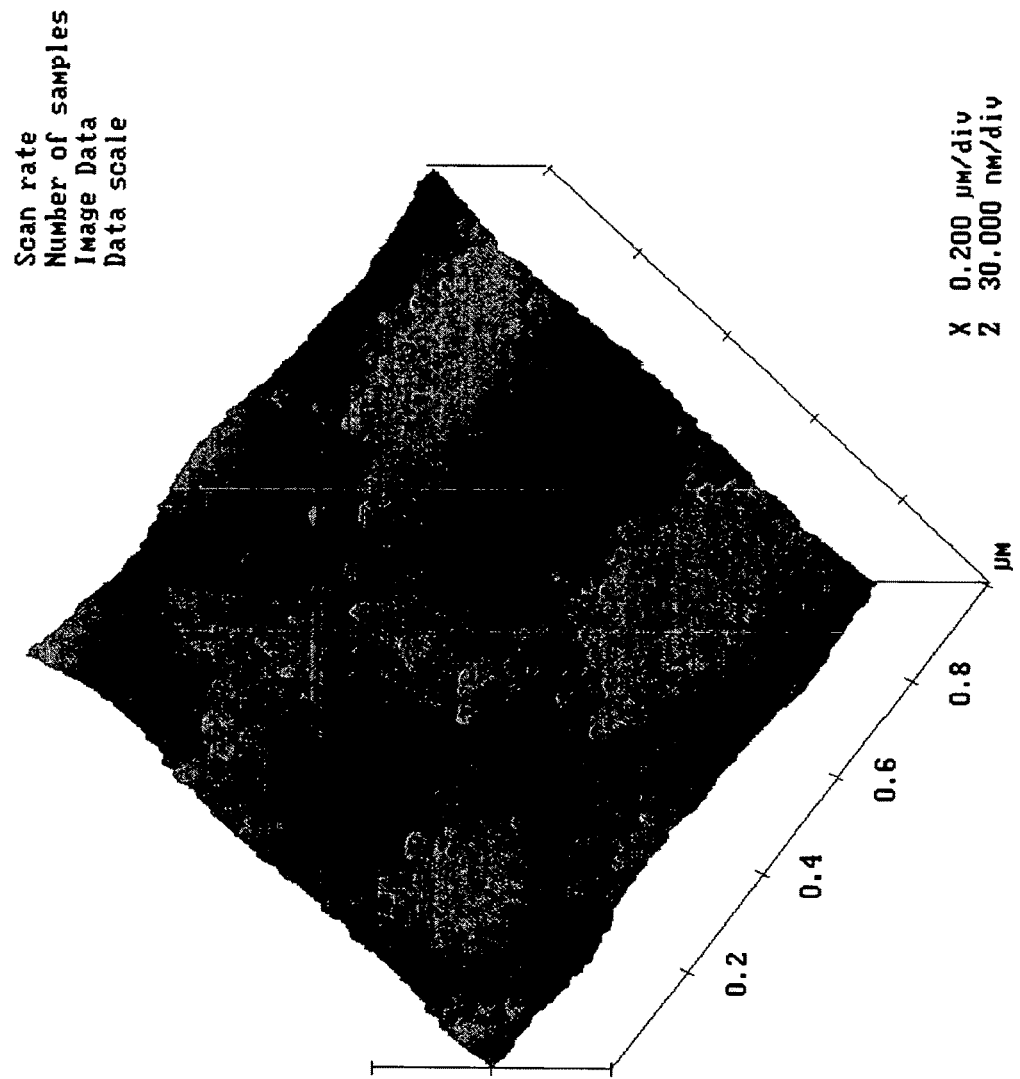
FIG. 8 is an AFM image showing the observation results of CyGDH immobilized to the surface of the phospholipid polymer layer using an AFM in Example 1.

As shown in FIG. 8, the surface of the phospholipid polymer layer Was formed with regularly arranged clusters (CyGDH) each having a diameter of about 6 to 30 nm. That is, CyGDH was immobilized to the phospholipid polymer in such a manner that at least part of CyGDH appeared on the surface. From the fact that the clusters are arranged regularly, it is presumed that CyGDH is immobilized to the phospholipid polymer layer with controlled orientation.

Example 2

In this example, responsiveness was examined with respect to an electrode (inventive electrode) to which CyGDH is immobilized via a phospholipid polymer layer and to an electrode (comparative electrode) to which CyGDH is immobilized without the intervention of a phospholipid polymer layer.

The inventive electrode was prepared by forming a phospholipid polymer layer on a carbon electrode and then immobilizing CyGDH, similarly to Example 1.

The comparative electrode was prepared similarly to the inventive electrode except that a phospholipid polymer layer was not formed.

Figure 9:
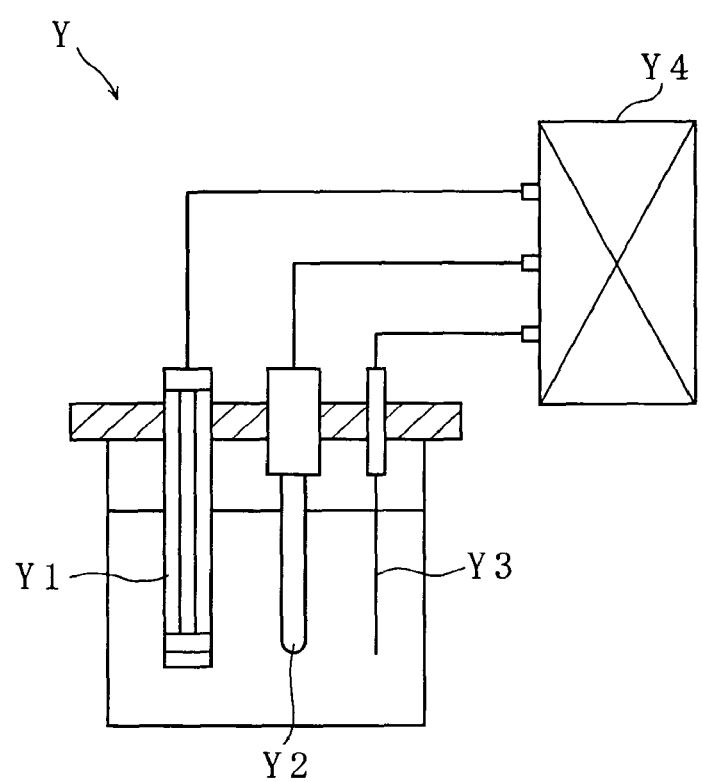
FIG. 9 is a schematic view showing the structure of a current measuring apparatus used in Example 2.

The responsiveness of the inventive electrode and the comparative electrode was evaluated as the responsive current obtained when a voltage was applied to a glucose solution using a current measuring apparatus Y prepared as shown in FIG. 9.

The current measuring apparatus Y includes a working electrode Y1, a reference electrode Y2 and a counter electrode Y2, which are connected to a potentiostat Y4. The current measuring apparatus Y is designed to measure the responsive current by immersing the electrodes Y1-Y3 in a glucose solution and applying a voltage to the glucose solution. Herein, the working electrode Y1 is the inventive electrode or the comparative electrode prepared in the above-described manner. The reference electrode Y2 is a silver-silver chloride electrode (Tradename "RE-1B"; available from BAS Inc.). The counter electrode Y3 is a platinum electrode.

(Linear Sweep Voltammetry)

In this example, before the responsiveness of the inventive electrode and the comparative electrode was evaluated, measurement by linear sweep voltammetry was performed with respect to glucose solutions of different concentrations using the current measuring apparatus X in which the inventive electrode was employed as the working electrode Y1.

In this measurement, the sweep voltage was 100 mV/sec, and the responsive current was measured with respect to the range of −400 mV to +700 mV. The glucose solutions had the concentrations of 0 mg/dL, 50 mg/dL, 100 mg/dL, 200 mg/dL, 400 mg/dL and 600 mg/dL, respectively. As a result, in the range of +100 to +700 mV, variation in responsive current in accordance with the difference in concentration of the glucose solutions was observed. Considering this result, in the subsequent responsive current measurement, the voltage to be applied to the glucose solutions was set to +600 mV.

(Responsiveness)

Figure 10:
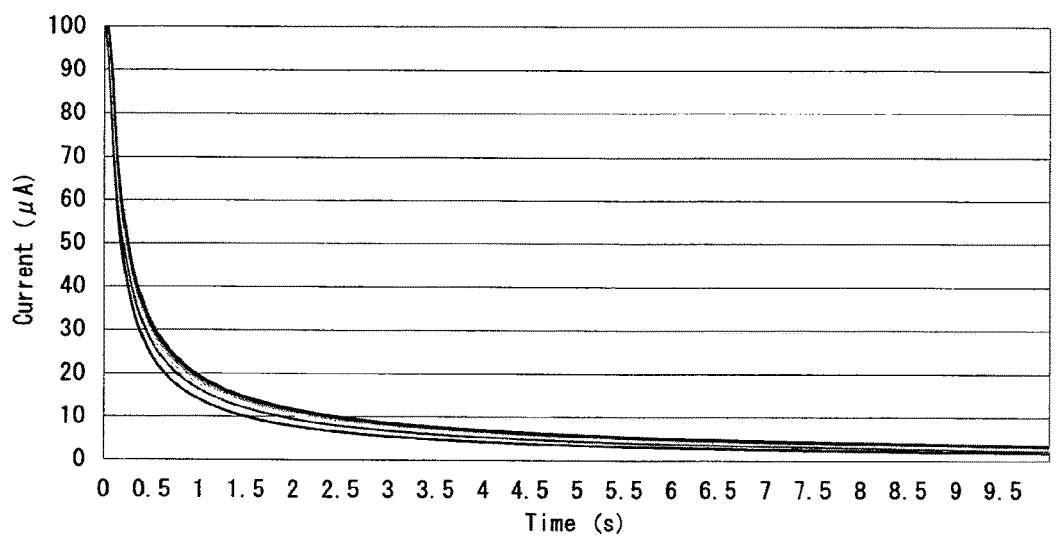
FIG. 10 is a graph showing the time-course measurements of the responsive current in Example 2.
Figure 10:
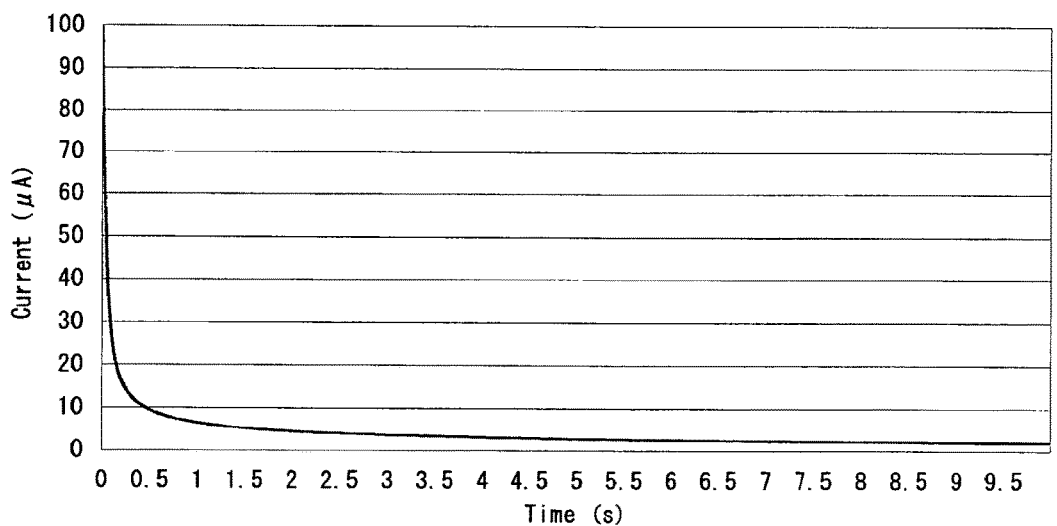

The responsiveness of the inventive electrode and the comparative electrode was evaluated by measuring the time course of the responsive current with respect to each of the glucose solutions of different concentrations. The measurement was performed using the above-described current measuring apparatus Y employing the inventive electrode or the comparative electrode as the working electrode Y1. As noted above, the voltage of +600 mV was applied in measuring the responsive current. The concentrations of the used glucose solutions were 0 mg/dL, 50 mg/dL, 100 mg/dL, 200 mg/dL, 400 mg/dL and 600 mg/dL, respectively. The time course of the responsive current with respect to each of the glucose solutions is shown in FIG. 10. The responsive current one second after the start of the measurement is shown in FIG. 11 in relation to the glucose level.

Figure 11:
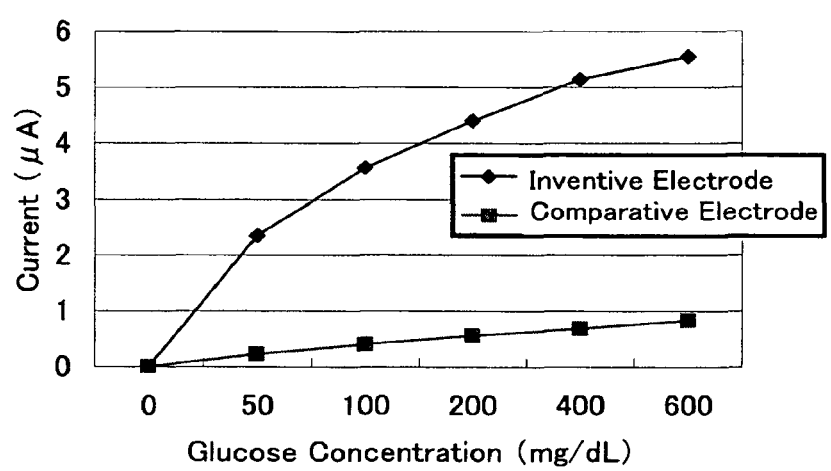
FIG. 11 is a graph showing the measurements of the responsive current in Example 2 in relation to glucose level.
Figure 12:
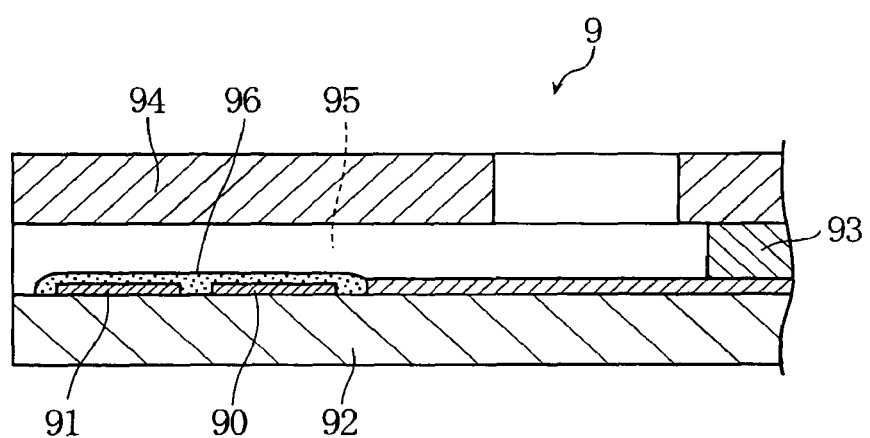
FIG. 12 is a sectional view showing a principal portion of an example of conventional biosensor.

As will be understood from FIGS. 10 and 11, when the inventive electrode was used, the responsive current in the µ order was measured. However, when the comparative electrode was used, merely the responsive current in the n order was measured. Specifically, the results obtained when the comparative electrode was used were similar to the conventionally reported measurement results (n order) of the responsive current obtained when use was made of a system which does not include an electron mediator such as a metal complex. When the inventive electrode was used, on the other hand, the responsive current in the µ order which was much higher than the conventionally reported level was measured. Thus, it is demonstrated that the inventive electrode has high responsiveness (sensitivity).

Moreover, as will also be understood from FIGS. 10 and 11, when the inventive electrode is used, the difference in glucose level is properly reflected as the difference in responsive current. Thus, by using the inventive electrode, the glucose level is measured properly at least in the glucose level range (0 to 600 mg/dL) with respect to which the responsive current was measured in this example.

As will be understood from the above, the inventive electrode in which CyGDH is immobilized via a phospholipid polymer layer has sufficient responsiveness (sensitivity) to properly measure the glucose level without using an electron mediator such as a metal complex. Thus, with the use of the inventive electrode, proper measurement of the glucose level (e.g. blood glucose level) without using an electron mediator is possible. Since an electron mediator is not used, to embed the inventive electrode in the human body for use causes no harm to the human body. Thus, the present invention is applicable to a biosensor to be embedded in the human body to monitor the blood glucose level.

The method for immobilizing CyGDH which is employed for the inventive electrode, i.e., the application of a phospholipid polymer solution and the immersion in a CyGDH solution is a very easy work. Thus, this method is applicable to a biosensor including minute paths such as μTAS. Since the phospholipid polymer layer and the CyGDH layer formed at the minute paths are extremely thin, the formation of these layers does not considerably hinder the movement of a sample in the minute paths. Thus, the provision of a reagent portion, which is made up of a phospholipid polymer layer and a CyGDH layer, at most part of the minute paths does not cause any problems. Thus, by forming a reagent portion over a wide range of the minute paths, the sensitivity of the μTAS, which has been disadvantageously low, is improved. In this way, a μTAS having a high sensitivity can be provided.

The invention claimed is:
1. A biosensor, comprising:
a substrate;
a capillary formed on the substrate for passage of a fluid to be analyzed;
an electrode formed on the substrate; and
a reagent portion formed on the substrate to cover the electrode;
wherein the reagent portion comprises:
an orientation-controlling layer formed on the electrode in contact therewith; and
a layer of protein that is immobilized on a side of the orientation-controlling layer opposite the electrode in direct contact with the orientation-controlling layer, the layer of protein containing a cytochrome or a cytochrome complex, and the cytochrome or cytochrome complex of the layer of protein being oriented toward the orientation-controlling layer; and
wherein the orientation-controlling layer contains a phospholipid polymer, the phospholipid polymer being 2-methacryloyloxyethyl phosphorylcholine polymer.

2. The biosensor according to claim 1, wherein the orientation-controlling layer contains a silane coupling agent for bonding the orientation-controlling layer to the electrode.

3. The biosensor according to claim 2, wherein the silane coupling agent is tetraethoxysilane.

4. The biosensor according to claim 1, wherein the layer of protein comprises cytochrome glucose dehydrogenase containing an α subunit having a glucose dehydrogenase activity and cytochrome C having a function of electron transfer, the cytochrome C of the layer of protein being oriented toward the orientation-controlling layer, and the α subunit of the layer of protein being oriented away from the orientation-controlling layer.

5. A biosensor, comprising:
a substrate;
a capillary formed on the substrate for passage of a fluid to be analyzed;
an electrode formed on the substrate; and
a reagent portion formed on the substrate to cover the electrode;
wherein the reagent portion comprises:
an orientation-controlling layer formed on the electrode in contact therewith; and
a layer of protein that is immobilized on a side of the orientation-controlling layer opposite the electrode in direct contact with the orientation-controlling layer, the layer of protein containing a cytochrome or a cytochrome complex, and the cytochrome or cytochrome complex of the layer of protein being oriented toward the orientation-controlling layer; and
wherein the orientation-controlling layer contains a silane coupling agent for bonding the orientation-controlling layer to the electrode.

6. The biosensor according to claim 5, wherein the orientation-controlling layer contains a phospholipid polymer.

7. The biosensor according to claim 5, wherein the silane coupling agent is tetraethoxysilane.

8. The biosensor according to claim 5, wherein the layer of protein comprises cytochrome glucose dehydrogenase containing an α subunit having a glucose dehydrogenase activity and cytochrome C having a function of electron transfer, the cytochrome C of the layer of protein being oriented toward the orientation-controlling layer, and the α subunit of the layer of protein being oriented away from the orientation-controlling layer.

9. A method for immobilizing a protein in a biosensor, the biosensor comprising:
a substrate;
a capillary formed on the substrate for passage of a fluid to be analyzed; and an electrode formed on the substrate;
the method comprising:
forming an orientation-controlling layer on a portion of the electrode in contact therewith; and
causing a layer of protein to immobilize on a side of the orientation-controlling layer opposite the electrode in direct contact with the orientation-controlling layer, the layer of protein containing cytochrome or a cytochrome complex, the cytochrome or cytochrome complex of the layer of protein being oriented toward the orientation-controlling layer; and
wherein the orientation-controlling layer contains a phospholipid polymer, the phospholipid polymer is 2-methacryloyloxyethyl phosphorylcholine polymer.

10. The protein immobilization method according to claim 9, further comprising subjecting said portion of the electrode to hydrophilic treatment before forming the orientation-controlling layer.

11. The protein immobilization method according to claim 10, wherein the orientation-controlling layer is formed to contain a silane coupling agent for bonding the orientation-controlling layer to the electrode.

12. The protein immobilization method according to claim 11, wherein the silane coupling agent is tetraethoxysilane.

13. The protein immobilization method according to claim 9, wherein the layer of protein comprises cytochrome glucose dehydrogenase containing an α subunit having a glucose dehydrogenase activity and cytochrome C having a function of electron transfer, the protein being immobilized on said portion of the electrode in a manner such that the cytochrome C of the layer of protein is oriented toward the orientation-controlling layer while the α subunit of the layer of protein is oriented away from the orientation-controlling layer.

14. The protein immobilization method according to claim 9, wherein the layer of protein is immobilized on the orientation-controlling layer by self-assembly.

15. A method for immobilizing a protein in a biosensor, the biosensor comprising:
   a substrate;
   a capillary formed on the substrate for passage of a fluid to be analyzed; and an electrode formed on the substrate;
   the method comprising:
   forming an orientation-controlling layer on a portion of the electrode in contact therewith; and
   causing a layer of protein to immobilize on a side of the orientation-controlling layer opposite the electrode in direct contact with the orientation-controlling layer, the layer of protein containing cytochrome or a cytochrome complex, the cytochrome or cytochrome complex of the layer of protein being oriented toward the orientation-controlling layer; and
   wherein the orientation-controlling layer is formed to contain a silane coupling agent for bonding the orientation-controlling layer to the electrode.

16. The protein immobilization method according to claim 15, wherein the orientation-controlling layer contains a phospholipid polymer.

17. The protein immobilization method according to claim 16, wherein the phospholipid polymer is 2-methacryloyloxyethyl phosphorylcholine polymer.

18. The protein immobilization method according to claim 15, further comprising subjecting said portion of the electrode to hydrophilic treatment before forming the orientation-controlling layer.

19. The protein immobilization method according to claim 15, wherein the silane coupling agent is tetraethoxysilane.

20. The protein immobilization method according to claim 15, wherein the layer of protein comprises cytochrome glucose dehydrogenase containing an α subunit having a glucose dehydrogenase activity and cytochrome C having a function of electron transfer, the protein being immobilized on said portion of the electrode in a manner such that the cytochrome C of the layer of protein is oriented toward the orientation-controlling layer while the α subunit of the layer of protein is oriented away from the orientation-controlling layer.

21. The protein immobilization method according to claim 15, wherein the layer of protein is immobilized on the orientation-controlling layer by self-assembly.

* * * * *